United States Patent [19]

Stone

[11] Patent Number: 5,573,534
[45] Date of Patent: Nov. 12, 1996

[54] BIPOLAR ELECTROSURGICAL INSTRUMENTS

[75] Inventor: Corbett Stone, Newtown, Conn.

[73] Assignee: United States Surgical Corporation, Norwalk, Conn.

[21] Appl. No.: 427,489

[22] Filed: Apr. 24, 1995

Related U.S. Application Data

[63] Continuation of Ser. No. 58,575, May 6, 1993, abandoned.

[51] Int. Cl.⁶ .................................................. A61B 17/38
[52] U.S. Cl. ............................................................. 606/48
[58] Field of Search ................................. 606/39, 41, 45, 606/46, 48, 51, 52

[56] References Cited

U.S. PATENT DOCUMENTS

| | | |
|---|---|---|
| 3,643,663 | 2/1972 | Sutter . |
| 3,799,168 | 3/1974 | Peters . |
| 3,920,021 | 11/1975 | Hiltebrandt . |
| 3,938,527 | 2/1976 | Rioux et al. . |
| 3,970,088 | 7/1976 | Morrison . |
| 3,987,795 | 10/1976 | Morrison . |
| 4,003,380 | 1/1977 | Wien . |
| 4,005,714 | 2/1977 | Hiltebrandt . |
| 4,014,343 | 3/1977 | Esty . |
| 4,016,881 | 4/1977 | Rioux et al. . |
| 4,033,351 | 7/1977 | Hetzel . |
| 4,034,762 | 7/1977 | Cosens et al. . |
| 4,041,952 | 8/1977 | Morrison, Jr. et al. . |
| 4,043,342 | 8/1977 | Morrison, Jr. . |
| 4,074,718 | 2/1978 | Morrison, Jr. . |
| 4,076,028 | 2/1978 | Simmons . |
| 4,161,950 | 7/1979 | Doss et al. . |
| 4,202,337 | 5/1980 | Hren et al. . |
| 4,228,800 | 10/1980 | Degler, Jr. et al. . |
| 4,232,676 | 11/1980 | Herczog . |
| 4,248,231 | 2/1981 | Herczog et al. . |
| 4,311,145 | 1/1982 | Esty et al. . |
| 4,314,559 | 2/1982 | Allen . |
| 4,333,467 | 6/1982 | Domicone . |
| 4,370,980 | 2/1983 | Lottick . |
| 4,418,692 | 12/1983 | Guny . |
| 4,481,057 | 11/1984 | Beard . |
| 4,483,338 | 11/1984 | Bloom et al. . |
| 4,532,924 | 8/1985 | Auth et al. . |
| 4,534,347 | 8/1985 | Taylor . |
| 4,545,375 | 10/1985 | Cline . |
| 4,589,411 | 5/1986 | Friedman . |
| 4,622,966 | 11/1986 | Beard . |
| 4,655,216 | 4/1987 | Tischer . |
| 4,657,016 | 4/1987 | Garito et al. . |

(List continued on next page.)

FOREIGN PATENT DOCUMENTS

| | | |
|---|---|---|
| 0 517 244 A1 | 12/1992 | European Pat. Off. . |
| 0518230 | 12/1992 | European Pat. Off. . |
| 2 310 137 | 12/1976 | France . |
| 2 680 314 A1 | 2/1993 | France . |

OTHER PUBLICATIONS

"BiCOAG® Forceps," Everest Medical Corp., ©1992, pp. 1–4.

*Primary Examiner*—Angela D. Sykes
*Assistant Examiner*—Samuel Gilbert

[57] ABSTRACT

A bipolar electrosurgical instrument is provided having a handle assembly, an elongated body portion, and a tool mechanism. The body portion comprises an outer tubular member and an inner rod member coaxially slidable within the outer tubular member. Attached to a distal end of the body portion is a tool mechanism. The tool mechanism includes pivotally connected jaw members operatively connected to the inner rod member for movement by the handle assembly between open and closed positions. Each jaw member is fabricated from insulating material and is provided with a conductive pathway. The conductive pathways are positioned to permit sparking between the pathways when the jaw members are open. As the jaw members are approximated, the insulating jaw member material blocks the electrical path between the conductive pathways to terminate electrical treatment of tissue positioned between the jaw members.

23 Claims, 8 Drawing Sheets

U.S. PATENT DOCUMENTS

| | | |
|---|---|---|
| 4,674,498 | 6/1987 | Stasz . |
| 4,674,499 | 6/1987 | Pao . |
| 4,681,105 | 7/1987 | Tritt . |
| 4,686,980 | 8/1987 | Williams et al. . |
| 4,732,149 | 3/1988 | Sutter . |
| 4,765,331 | 8/1988 | Petruzzi et al. . |
| 4,785,807 | 11/1988 | Blanch . |
| 4,802,476 | 2/1989 | Noerenberg et al. . |
| 4,823,791 | 4/1989 | D'Amelio et al. . |
| 4,850,353 | 7/1989 | Stasz et al. . |
| 4,862,890 | 9/1989 | Stasz et al. . |
| 4,890,610 | 1/1990 | Kirwan, Sr. et al. . |
| 4,985,030 | 1/1991 | Melzer et al. . |
| 5,026,370 | 6/1991 | Lottick . |
| 5,049,148 | 9/1991 | Mehl ................... 606/52 X |
| 5,080,660 | 1/1992 | Buelna . |
| 5,116,332 | 5/1992 | Lottick . |
| 5,147,357 | 9/1992 | Rose et al. . |
| 5,147,378 | 9/1992 | Markham . |
| 5,151,102 | 9/1992 | Kamiyama et al. . |
| 5,171,311 | 12/1992 | Rydell et al. . |
| 5,197,964 | 3/1993 | Parins . |
| 5,217,458 | 6/1993 | Parins ................... 606/48 |
| 5,254,117 | 1/1993 | Rigby et al. ................... 606/46 |
| 5,258,006 | 11/1993 | Rydell et al. . |
| 5,281,220 | 1/1994 | Blake, III ................... 606/52 X |
| 5,391,166 | 2/1995 | Eggers ................... 606/48 |

FIG. 1

FIG_4

FIG_5

FIG_6

FIG_10

FIG_11

FIG_12

FIG_13

FIG. 19

BIPOLAR ELECTROSURGICAL INSTRUMENTS

This is a continuation of copending application Ser. No. 08/058,575 filed on May 6, 1993 now abandoned.

BACKGROUND OF THE INVENTION

1. Field of the Invention

The invention relates to bipolar electrosurgical instruments and, more particularly, to bipolar instruments for selectively grasping, manipulating, cutting and/or coagulating body tissue.

2. Description of the Related Art

Electrosurgery involves the cutting and/or coagulating of body tissue by application of high frequency electrical current. In bipolar electrosurgery, the electrical current is applied through an electrode which contacts the body tissue to be treated. A return electrode is placed in contact with or in close proximity to the current-supplying electrode such that an electrical circuit is formed between the two electrodes. In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

To perform tissue cutting and/or coagulation, a high frequency power supply is connected to the bipolar instrument. Each electrode of the bipolar instrument is electrically isolated within the instrument and is separately connected to the high frequency power supply. Typical power supplies such as the SSE2L™ available from Valleylab, Inc. of Boulder, Colo., are r.f. generators which can produce different electrical waveforms to effect various electrosurgical procedures.

A waveform of continuous sinewaves alternating from positive to negative at the operating frequency of the r.f. generator is employed to cut tissue. Such a waveform creates short, intense electrical sparks to rapidly heat tissue; cells are exploded and the heat dissipated as steam.

A waveform consisting of pulsating sine waves alternating from positive to negative at the operating frequency of the r.f. generator is employed to coagulate tissue. Such a waveform creates longer, less intense sparks which heat tissue less rapidly, allowing heat to be dissipated more widely than during cutting. A combination of the cutting and coagulating waveforms produces the capability to cut tissue with enhanced hemostasis over the pure cutting waveform.

A fuller description concerning the electrical aspects of electrosurgery can be found in the Valleylab SSE2L™ Instruction Manual published by Valleylab of Boulder, Colo., the disclosure of which is incorporated herein by reference.

Electrosurgical procedures have, in recent years, become increasingly widespread. The ease and speed of cutting and/or coagulating tissue saves the surgeon valuable time while minimizing internal bleeding by the patient. Endoscopic and laparoscopic surgical procedures have created additional incentives for the use of electrosurgical techniques. In laparoscopic procedures, surgery is performed in the interior of the abdomen through a small incision; in endoscopic procedures, surgery is performed in any hollow viscus of the body through narrow tubes inserted through small entrance wounds in the skin. Because laparoscopic and endoscopic surgery do not bring the surgeon into direct contact with the operation site, internal bleeding must be quickly controlled by instruments easily operable from a remote location. Electrosurgical instruments provide the surgeon with the ability to electrically cut tissue such that bleeding is minimized and to effectively seal off bleeders during laparoscopic and endoscopic procedures.

Several configurations have been proposed for bipolar electrosurgical instruments particularly adapted for treating tissue. Bipolar knives are described in U.S. Pat. Nos. 4,161,950 and 4,232,676. In these patents, two or more separated, fixed electrodes are disposed on the surface of a ceramic blade. These electrodes are used to cut and/or coagulate tissue when electrical current passes through tissue positioned between a pair of these fixed electrodes.

Another bipolar electrosurgical instrument is the bipolar forceps. This instrument, examples of which are described in U.S. Pat. Nos. 3,643,663 and 4,003,380, is used to treat tissue held between the conductive forceps jaws. Current flows through tissue held between the forceps jaws to effect cutting and/or coagulation of the tissue.

Other designs for bipolar forceps have been proposed. In U.S. Pat. No. 5,151,102, a sintered, insulating blood vessel contact member is provided on stainless steel or titanium forceps. Exposed electrodes of a conductive resin are disposed over the surface of the vessel contact member.

The product literature for EVERS HEARS®, available from Everest Medical Corporation, Minneapolis, Minn., describes laparoscopic scissors. Ceramic blades and a single-action dissecting tip are illustrated.

In all of the instruments described above, approximation of the jaws, or, in the case of bipolar knives and probes, the fixed relative position of the electrodes, creates an electrical circuit. As long as electrical current is supplied to the instrument and material capable of transporting the current, e.g., tissue, fluid, or ionized air, is positioned between the electrodes, current will flow and an electrical circuit will be maintained.

When both jaws are fabricated from electrically conductive material, as in the prior art, a bipolar electrosurgical instrument is not capable of automatic circuit interruption when the jaws are fully approximated. The user must either turn the instrument off or allow electrical treatment to proceed until tissue positioned between the jaws is no longer capable of conducting an electrical current.

Prior bipolar forceps, scissors, and the like additionally employ a substantial quantity of high thermal conductivity materials, such as metals, in jaw construction. The use of these materials causes the jaw members to heat substantially, even when portions of the jaws use insulating materials. This heating is undesirable in many surgical procedures.

A need exists in the art for bipolar electrosurgical instruments having jaw members employing minimal amounts of thermally conductive materials. A need also exists in the art for improved bipolar electrosurgical instruments in which an electrical circuit is formed as the instrument's jaws are approximated. Such instruments could be advantageously used to electrically treat tissue by cutting, coagulation, or a combination of cutting and coagulation.

SUMMARY OF THE INVENTION

The bipolar electrosurgical instrument of the present invention overcomes the disadvantages of previous instruments by employing jaw members fabricated from electrically insulating material. Conductive pathways formed in the jaw members serve as the bipolar electrodes. Preferably, the volume ratio of conductive to insulating material in the jaw members is less than about 50%. The conductive pathways preferably cover less than about 30% of the surface area of the jaw members.

In a preferred embodiment, the bipolar electrosurgical instrument of the present invention comprises a handle assembly, an elongated body portion, and a tool mechanism having first and second jaw members cooperating with a distal end of the body portion. The handle assembly may include a stationary handle and pivoting handle, the body portion being attached to the stationary handle and extending distally from the handle assembly.

The body portion comprises an outer tubular member and an inner rod member coaxially slidable within the outer tubular member. The rod member is attached to the pivoting handle, while the outer tubular member is secured to the stationary handle. As the pivoting handle moves, the rod member slidably reciprocates within the outer tubular member.

Attached to a distal end of the body portion is the tool mechanism which opens and closes in response to movement of the pivoting handle in relation to the stationary handle. One or both jaw members open and close to perform various surgical procedures. The jaw members may include, but is not limited to, a scissors device, a dissecting device, a grasping device and the like.

In one embodiment the jaw members are secured to the outer tubular member by means of a transverse post member which serves as a pivot point. One jaw member is stationary and the other jaw member is movable. The stationary jaw is provided with a longitudinal guide slot while the movable jaw is provided with an angled camming slot. In another embodiment, each jaw member is movable and is provided with an angled camming slot.

The inner rod member is provided with a bearing post member which passes through and is engaged within the longitudinal slot and the camming slot of the respective jaw members, or, alternatively, within the angled camming slot of each jaw member. As the pivoting handle is moved, the rod slides through the outer tube and causes the post member to bear on the camming slot to pivot a jaw member or members about the pivot point to open the jaw mechanism. As the rod reciprocates, the jaw mechanism opens and closes.

An electrical connection region in the handle assembly comprising a pair of electrical connection receptacles communicates with the outer tube and the inner rod respectively to provide two electrically isolated pathways through which current may flow.

In a preferred embodiment, the position of the respective conductive pathways permits sparking between the pathways when the jaw members are open. As the jaw members are approximated, the insulating jaw member material blocks the electrical path between the conductive pathways along the length of the jaw members. This configuration automatically terminates electrical treatment of tissue positioned between the jaw members.

A further feature of the present invention is the provision of a rotatable knob on the handle assembly to position the jaws at a desired rotational orientation with respect to the longitudinal axis during the surgical procedure. Preferably, the rotatable knob is secured to the outer tube and positioned in a slot which passes through the stationary handle, so that a surgeon may hold the instrument and rotate the knob, and consequently the body assembly and jaw mechanism, with one hand. This frees the surgeon's other hand to simultaneously operate another instrument during surgery.

BRIEF DESCRIPTION OF THE DRAWINGS

FIG. 7a is a frontal view of a pivot bushing for use with a bipolar electrosurgical instrument of the present invention.

FIG. 7b is a side view of the pivot bushing of FIG. 7a.

FIG. 8 is a side elevational view in partial cross-section of another preferred embodiment of the bipolar electrosurgical instrument of the present invention.

DETAILED DESCRIPTION OF THE PREFERRED EMBODIMENTS

In describing the bipolar electrosurgical instrument of the present invention, the term "distal" refers to a direction away from the instrument user and the term "proximal" refers to a direction towards the user, opposite to the distal direction. The term "endoscopic" is broadly used to indicate both laparoscopic and endoscopic procedures as well as instruments which are controlled remotely from the surgical site, usually through a narrow incision in the patient's body, cannula, or through a body orifice.

Figure 1:
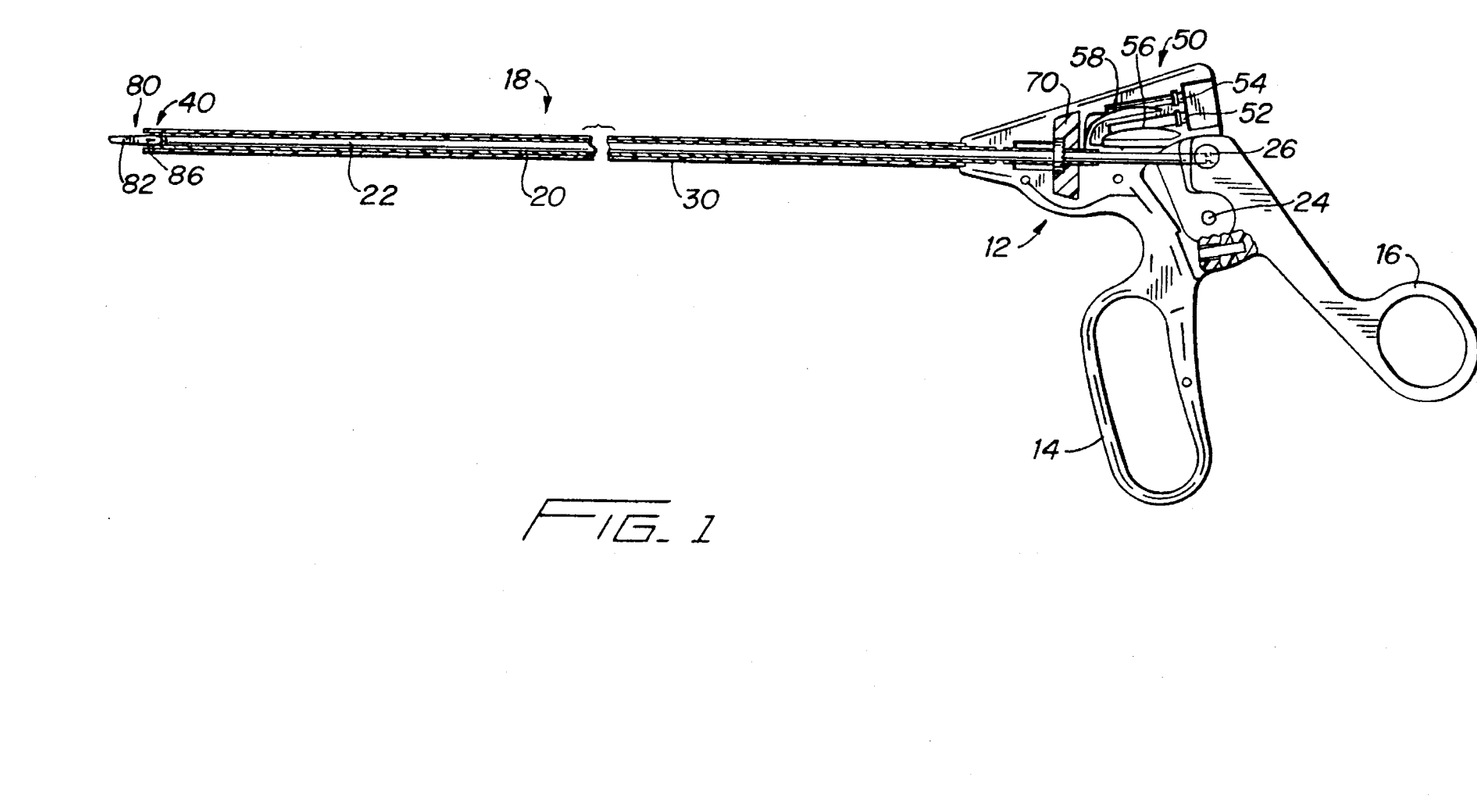
FIG. 1 is a side elevational view in partial cross-section of a bipolar electrosurgical instrument according to one preferred embodiment of the present invention.

Referring now in specific detail to the drawings, in which like reference numbers identify similar or identical elements, FIG. 1 illustrates a preferred embodiment of the bipolar electrosurgical instrument 10. The device comprises a handle assembly 12 which consists of a stationary handle 14 and a pivoting handle 16. Extending from the handle assembly is an elongated body portion 18 which comprises an outer tubular member 20 through which a slidable inner rod member 22 passes in coaxial relationship. Preferably, the elongated body portion is configured and dimensioned such that the instrument is adapted for endoscopic use. The outer tube 20 is secured to the stationary handle 14, while the inner rod 22 is secured to pivoting handle 16 at rotatable connection point 26. Handle 16 pivots about pivot point 24 to move in relation to stationary handle 14.

Attached at a distal end of the body portion 18 is a tool mechanism 80, which comprises a pair of jaw members 82 and 84, best seen in FIGS. 2–5. Jaw members 82 and 84 may comprise scissors, dissecting jaws, a grasping mechanism, or any other tool mechanism required for a bipolar electrosurgical procedure. The tool mechanism is connected to the outer tube 20 at pivot point 86 and moves in a reciprocating manner about pivot point 86 through the mechanism described below.

The handle assembly 12 may further include rotatable knob 70 to selectively position tool mechanism 80 to any rotational orientation about the longitudinal axis of the instrument. The positioning of the rotatable knob on the stationary handle allows the surgeon to hold the electrosurgical instrument 10 and rotate the knob with the same hand, leaving the other hand free to control another surgical instrument.

As knob 70 is rotated, the outer tube 20 is rotated therewith. Rotation of the outer tube consequently rotates pivot point 86 and with it, tool mechanism 80. Rotation of the tool mechanism causes rotation of inner rod 22, which is accomplished within rotatable connection point 26.

Figures 7A, 7B, 8:
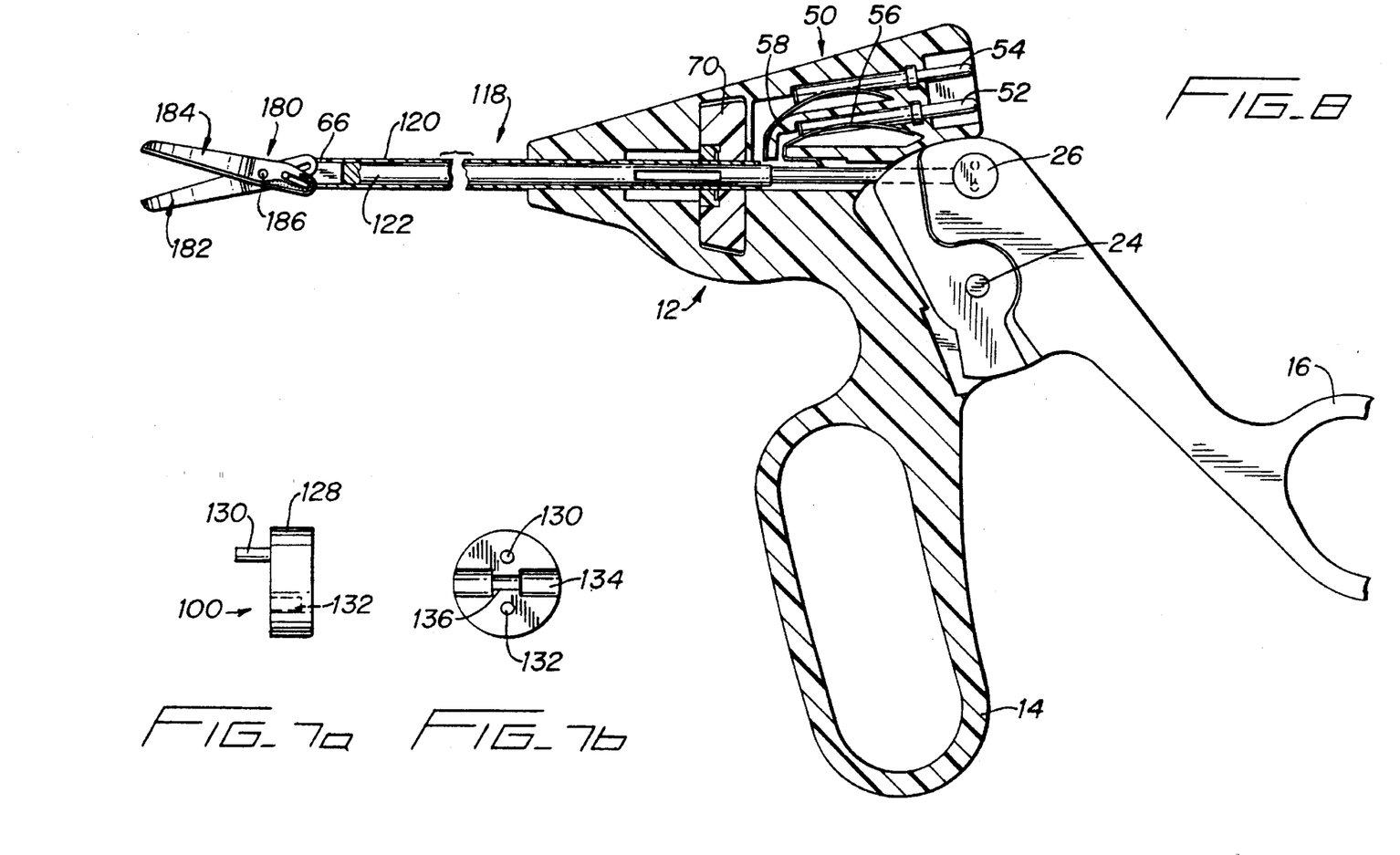

Rotatable connection point 26 comprises a pivot bushing 100, best seen in FIGS. 7a and 7b. Pivot bushing 100 is comprised of a pair of discs 128 each having a post member 130 and a hole 132 formed therein for interengaging the discs with each other. Groove 134 includes a notch portion 136 for accepting the end of rod member 22 which is formed with a corresponding notch. This notch secures rod 22 in place for longitudinal movement, while at the same time allowing for rotational movement.

The bushing 100 pivots during movement of pivoting handle 16 so that as rod member 22 is reciprocated within tube 20, the bushing member 100 pivots to minimize or eliminate any radial movement of rod 22, insuring that rod 22 moves in a longitudinal direction only. This alleviates excessive torquing forces on rod member 22 as well as unwanted excessive forces at the connection point 26, preventing damage to the handle or the inner rod member 22.

To provide electrical connection between tool mechanism 80 and a suitable r.f. power supply, electrical connection region 50 is provided in handle assembly 12. Electrical connection region 50 comprises a pair of electrical connection receptacles 52 and 54, illustratively depicted as a pair of female jacks. Leaf spring 56 connects receptacle 52 to inner rod 22 while leaf spring 58 connects receptacle 54 to outer tube 20. Both outer tube 20 and inner rod 22 are fabricated from suitable conductive materials such as stainless steel. This configuration provides two electrically isolated pathways through which current may flow, as required in bipolar applications.

An insulation member 30 is provided on outer tube 20. The insulation member preferably comprises heat shrink tubing which passes into stationary handle 14. The inner rod member may also be covered with a suitable insulating material to prevent arcing between the inner rod and the outer tube during instrument operation. To further insulate the instrument from the user, the handle may be constructed from a lightweight, rigid, plastic insulating material such as LEXAN™ polycarbonate, available form the General Electric Corporation.

Figure 2:
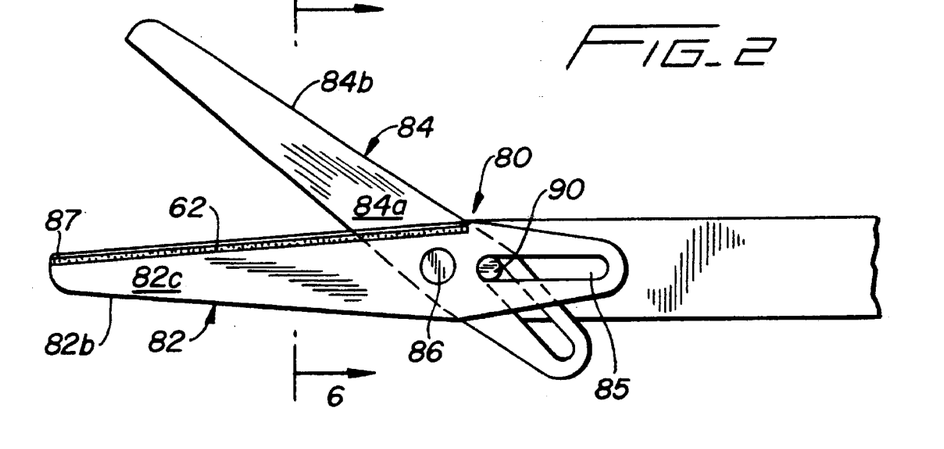
FIG. 2 is an enlarged right side view of a tool mechanism of the bipolar electrosurgical instrument of FIG. 1.
Figure 3:
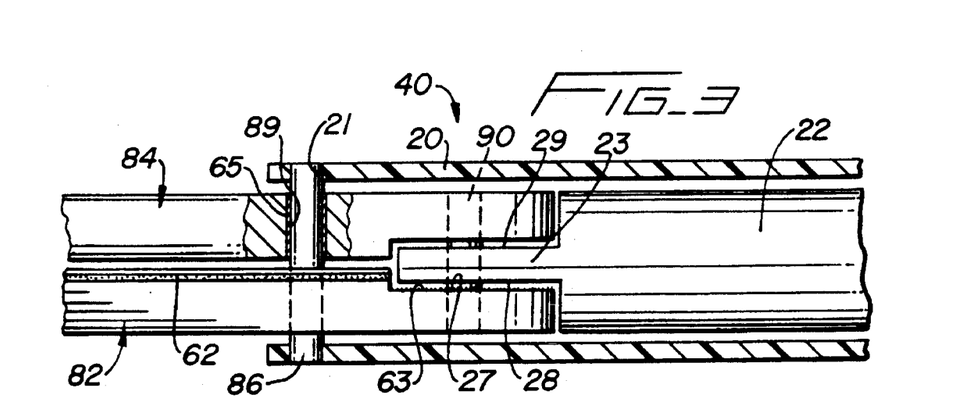
FIG. 3 is an enlarged top cutaway view of the tool mechanism of FIG. 2.

FIG. 2 is an enlarged view of the distal end of instrument 10 of FIG. 1 showing a preferred tool mechanism comprising scissors 80 having scissors blades 82 and 84. Scissors blades 82 and 84 are respectively provided with an exterior edge 82b and 84b, as well as angled cutting surfaces 87 and 88, shown in FIG. 6. Scissors blade 84 is provided with an interior surface 84a and an outer surface (not shown) opposite the interior surface. Scissors blade 82 is provided with an exterior surface 82c and an interior surface (not shown) opposite the exterior surface. Stationary scissors blade 82 is pivotally connected to movable scissors blade 84 about transverse pivot pin 86. As shown in FIG. 3, transverse pin 86 is attached to the distal end of outer tubular member 20 through aperture 21.

Mechanism 40 connects the tool mechanism to the handles as shown in FIG. 3. Inner rod 22 terminates at its distal end in portion 23 having flat surfaces 28 and 29. A transverse bearing post 90 is attached to inner rod 22 through aperture 27 and is adapted for longitudinal reciprocal motion with the inner rod. A longitudinal slot 83 is provided in a proximal end of stationary blade 82 in an area proximal to and in longitudinal alignment with transverse pivot pin 86. Bearing post 90 interfits with slot 83 for longitudinal reciprocal motion therein and serves to prevent pivotal motion of blade 82 about pivot pin 86.

An angled cam slot 85 is provided in a proximal end of movable blade 84 in an area proximal to transverse pivot pin 86. Bearing post 90 interfits within angled cam slot 85 and serves to translate the longitudinal motion of inner rod 22 relative to outer tube 20 into pivotal motion of blade 84 about pivot pin 90. Through this configuration, distal movement of transverse bearing post 90 from its initial proximal position causes blade 84 to be cammed open relative to blade 82 which remains oriented along the same longitudinal axis as inner rod 22. Correspondingly, proximal movement of rod 22 causes bearing post 90 to cam blade 84 to a closed position as shown in FIG. 1.

Figure 6:
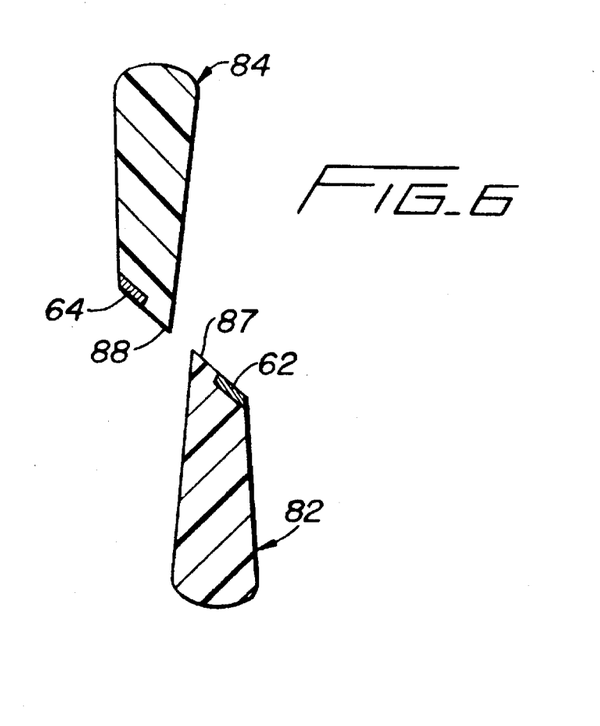
FIG. 6 is a cross-sectional view of the two blade members taken along line 6—6 of FIG. 2 illustrating the relation of the conductive pathways to each other.

Blades 82 and 84 are fabricated from an insulating material and are provided, respectively, with conductive pathways 62 and 64 preferably disposed on the angled cutting surfaces of the blades, best seen in FIG. 6. Other positions for the conductive pathways on blades 82 and 84 are also suitable and within the scope of the invention.

Figure 5:
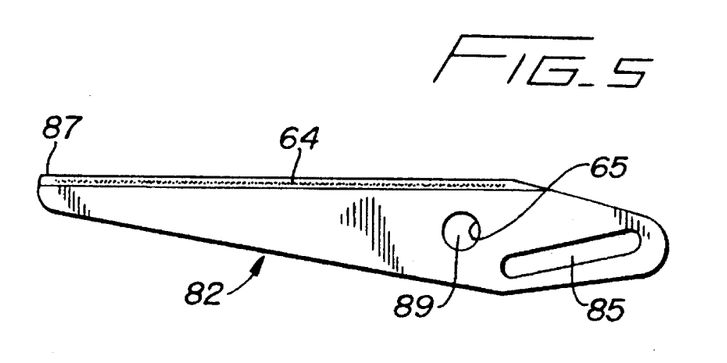
FIG. 5 is a left side view of a second jaw member of the tool mechanism of FIG. 2.

The conductive pathways receive electrical energy from the power source and function as the electrodes of the instrument. The conductive pathways may terminate proximal to the distal end of the blades, as shown in FIGS. 2 and 5. In a preferred embodiment, the conductive pathways are formed within grooves on the angled cutting surfaces of the scissors blades, depicted in FIG. 6. Disposing the conductive pathways within grooves permits formation of a conductor surface flush with the remainder of the blade. Advantageously, blade movement is the same as in instruments having blades formed from a single material.

In a preferred embodiment, the position of conductive pathways 62 and 64 on the blades 82 and 84 permits sparking between the pathways when the blades are open. However, as the blades are approximated, the insulating blade material blocks the electrical path between conductive pathways 62 and 64 along the length of the blades. This configuration automatically terminates electrical treatment of tissue positioned between the blades.

Figure 2A:
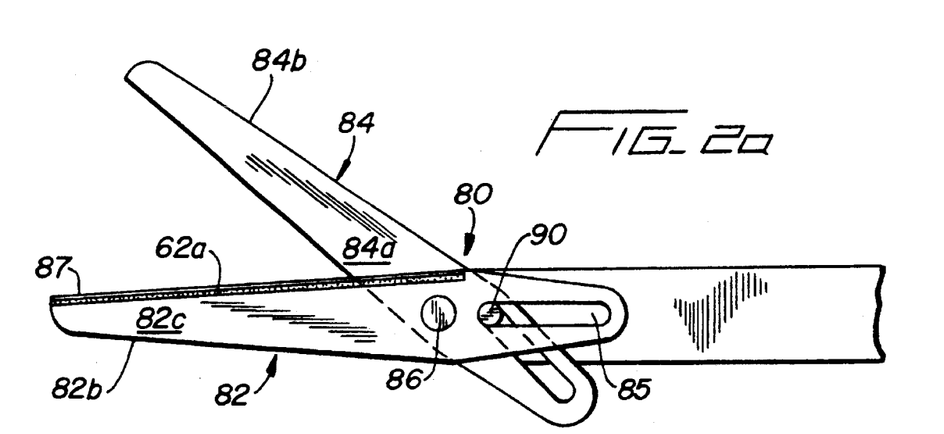
FIG. 2a is an enlarged right side view of an alternate embodiment of a tool mechanism of a bipolar electrosurgical instrument according to the present invention.

In the alternate embodiment of FIG. 2b, the conductive pathways 62a and 64a extend to the distal end of the blade members. When the conductive pathways extend to the distal end of the instrument, sparking may still occur at the fully approximated blade tips. This configuration advantageously permits electrical treatment of small tissue areas adjacent the instrument tip, e.g., spot coagulation or dissection.

Conductive pathways 62 and 64 may be formed such that their exposed surface area is significantly smaller than the surface area of blades 82 and 84. Preferably, the surface area of a conductive pathway strip is less than 30% of the area of the insulating blade upon which it is disposed. Additionally, the conductive pathways may be substantially thinner than the blade members. As such, the total volume of conductive material is less than the total volume of insulating material forming the blades. Preferably the volume of conductive material is less than 50% of the volume of the insulating material, and more preferably, less than 20%. By minimizing the surface area and volume of conductive material, heating of the blade assembly is substantially reduced. Consequently, undesirable effects such as tissue adherence to the blade surface, or heating of adjacent tissue structures is reduced.

Figure 4:
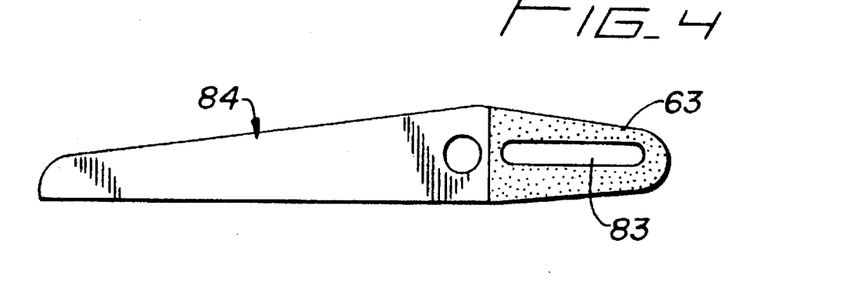
FIG. 4 is a right side view of a first jaw member of the tool mechanism of FIG. 2.

Conductive pathways 62 and 64 respectively communicate with inner rod 22 and outer tube 20 through conductive regions 63 and 65. Region 63, shown in FIGS. 3 and 4, is located adjacent surface 28 of conductive inner rod 22. In use, current flows from rod 22 through region 63 and along conductive path 62. Region 65, shown in FIGS. 3 and 5, is located on the surface of through hole 89 of blade 84. Pivot pin 86, fabricated form a suitable conducting material such as stainless steel, provides a path for current flow from outer tube 20. Current flows from outer tube 20 through pivot pin 86. Pivot pin 86, traverses through-hole 89, transmits power through conductive region 65 plated on the interior of hole 89. Conductive region 65 is connected to conductive path 64.

Referring to FIG. 8, another embodiment of the bipolar electrosurgical instrument of the present invention is shown. Handle assembly 12, electrical connection region 50, rotating knob 70, and rotatable connection point 26 are all substantially similar to the corresponding elements of the previous embodiment.

Extending from the handle assembly is an elongated body portion 118 which comprises an outer tubular member 120 through which a slidable inner rod member 122 passes in coaxial relationship.

Figure 9A:
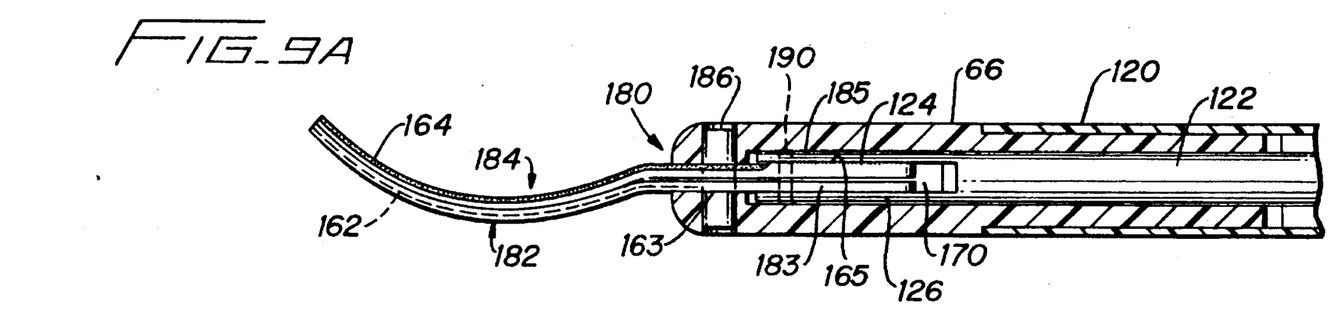
FIG. 9A is a top view in partial cross section of the tool mechanism of the bipolar electrosurgical instrument of FIG. 8 in a closed position.
Figure 9B:
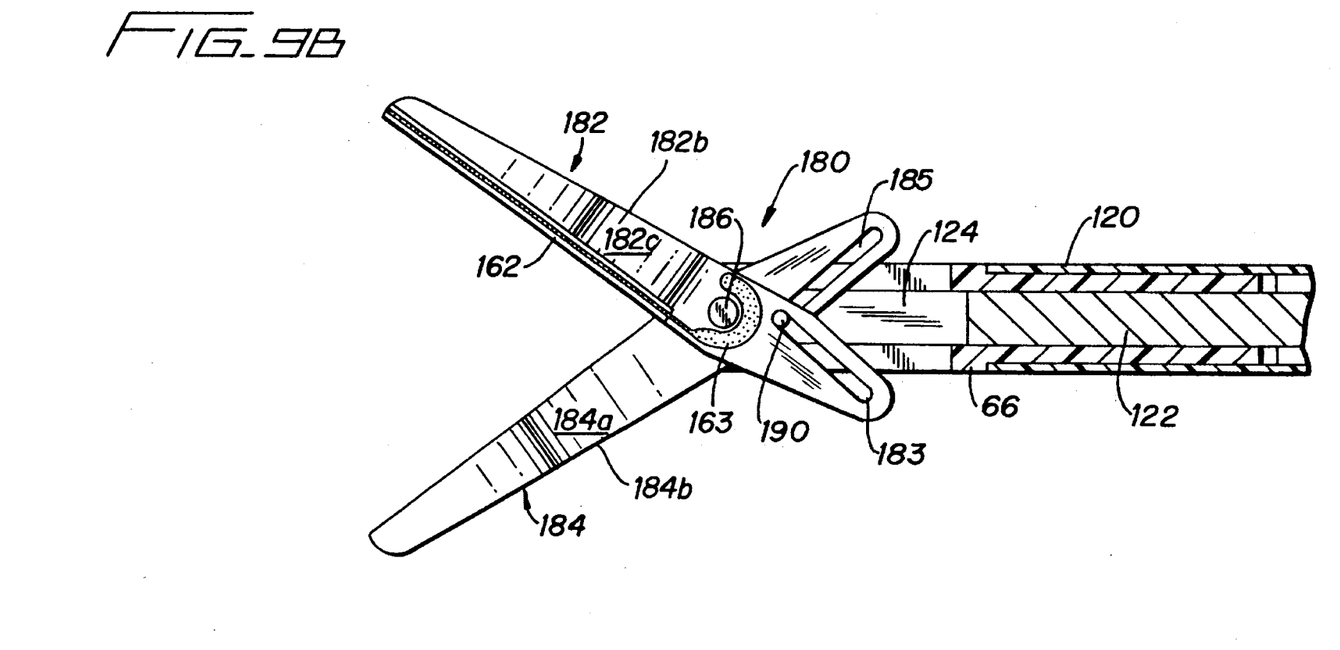
FIG. 9B is a side view in partial cross section of the tool mechanism of FIG. 9A in an open position.

Attached at a distal end of the body portion 118 is tool mechanism 180, best seen in FIG. 9, which comprises a pair of jaw members 182 and 184, best seen in FIGS. 10–13. Jaw members 182 and 184 are respectively provided with an exterior edge 182b and 184b as well as angled cutting surfaces. Jaw member 184 is provided with an interior surface 184a and an outer surface (not shown) opposite the interior surface. Jaw member 182 is provided with an exterior surface 182c and an interior surface (not shown) opposite the exterior surface. Jaw members 182 and 184 are illustratively depicted as curved scissors blades, but may comprise any tool mechanism used in an electrosurgical procedure.

Figure 14A:
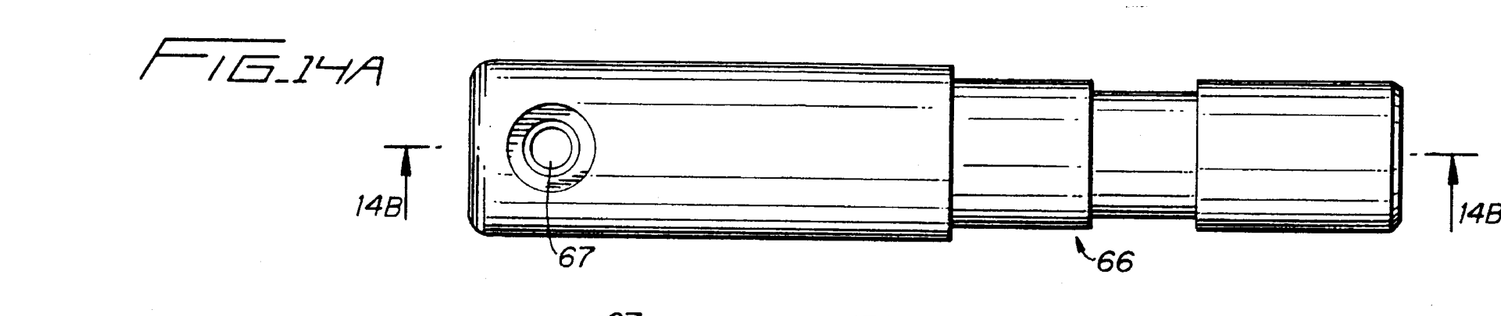
FIG. 14A is a side view of a housing member of the bipolar electrosurgical instrument of FIG. 8.
Figure 14B:
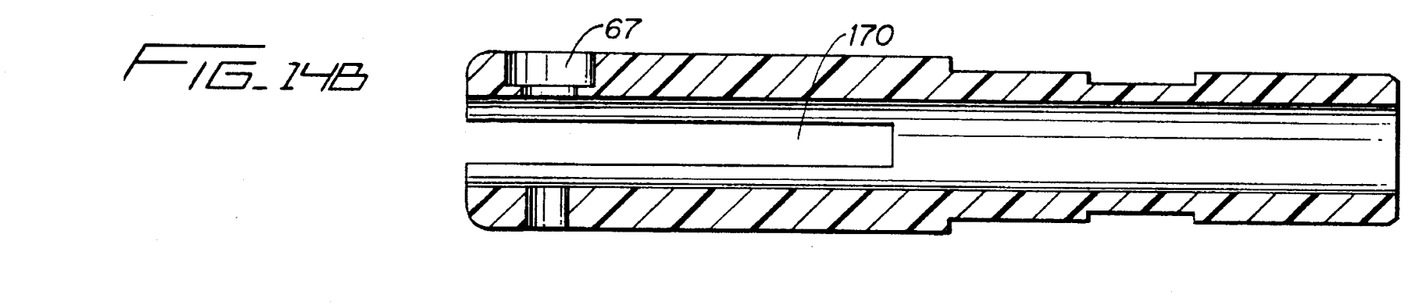
FIG. 14B is a top cutaway view along line A—A of FIG. 14A.

In the embodiment of FIG. 8, tool mechanism 180 is attached to outer tube 120 through housing member 66. Housing member 66 is shown in detail in FIGS. 14A and 14B, in which a diametric radial hole 67 is provided to accept pivot pin 186 to allow the jaw members to pivot about pin 186 during opening and closing. Housing member 66 is provided with a longitudinal slot 170 which allows scissors blades 182 and 184 to open and close.

Figure 10:
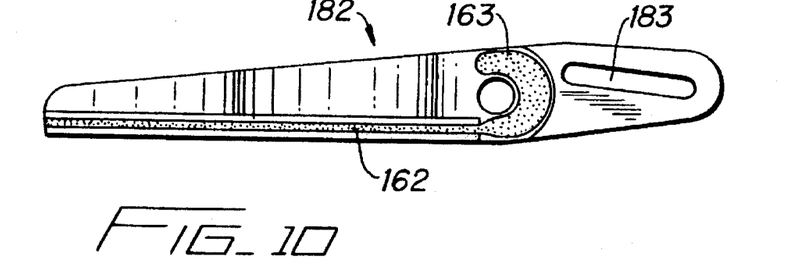
FIG. 10 is a side view of a first jaw member of the tool mechanism of the bipolar electrosurgical instrument of FIG. 8.
Figure 11:
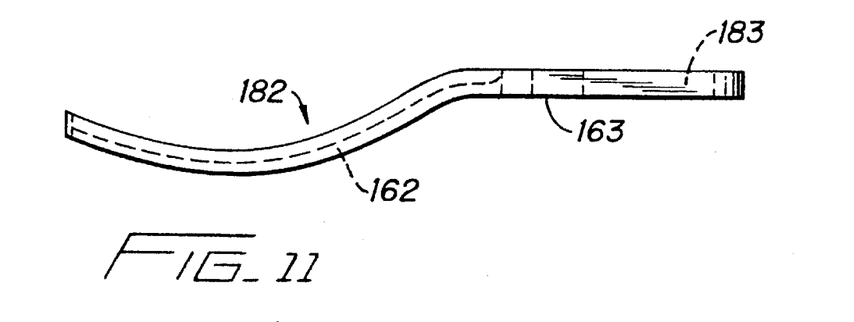
FIG. 11 is a top view of the jaw member of FIG. 10.
Figure 12:
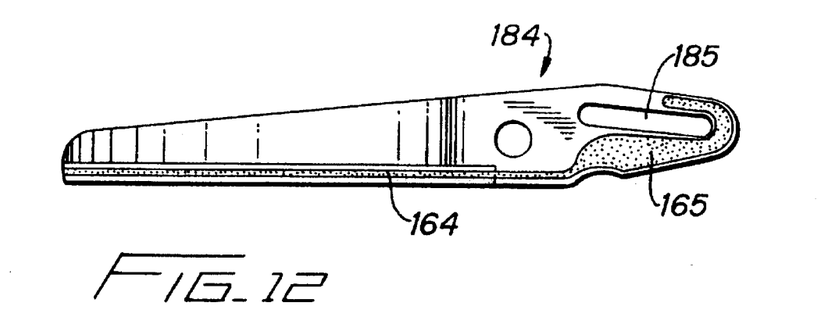
FIG. 12 is a side view of a second jaw member of the tool mechanism of the bipolar electrosurgical instrument of FIG. 8.
Figure 13:
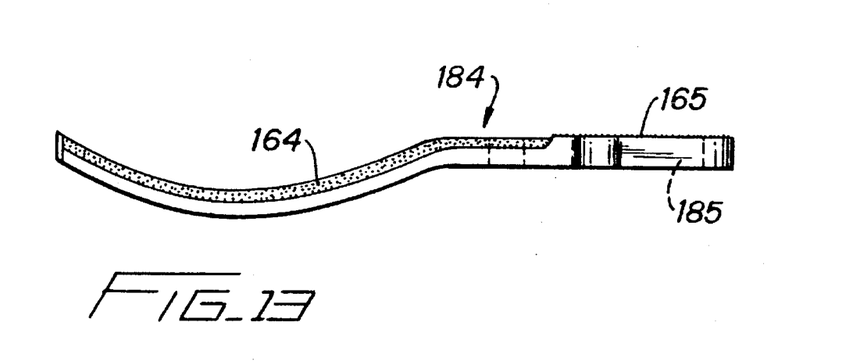
FIG. 13 is a top view of the jaw member of FIG. 12.

Inner rod 122 divides into arms 124 and 126 at its distal end, enabling the proximal ends of scissors blades 182 and 184 to pass therebetween. Angled camming slots 183 and 185, best seen in FIGS. 9B, 10, and 12, are respectively provided in blades 182 and 184 to permit both blades 182 and 184 to be moved between open and closed positions. These camming slots accept a bearing post 190 which is attached to arms 124 and 126 of inner rod 122.

Curved scissors blades 182 and 184, fabricated from an insulating material as in the previous embodiment, are provided, respectively, with conductive pathways 162 and 164 disposed on the angled cutting surfaces of the blades. Pathway 162 communicates with housing 66 through conductive region 163 adjacent pivot pin 186. A conductive washer (not shown) may be included to further ensure electrical contact between pin 186 and conductive region 163. Housing 66 cooperates with outer tube 120 to provide communication between electrical contact region 50 and pathway 162.

Conductive pathway 164 communicates with arm 124 of inner rod 122 through conductive region 165. Current flows from the inner rod of the housing member through conductive region 165 and along conductive pathway 164, as in the previous embodiment.

Figure 15:
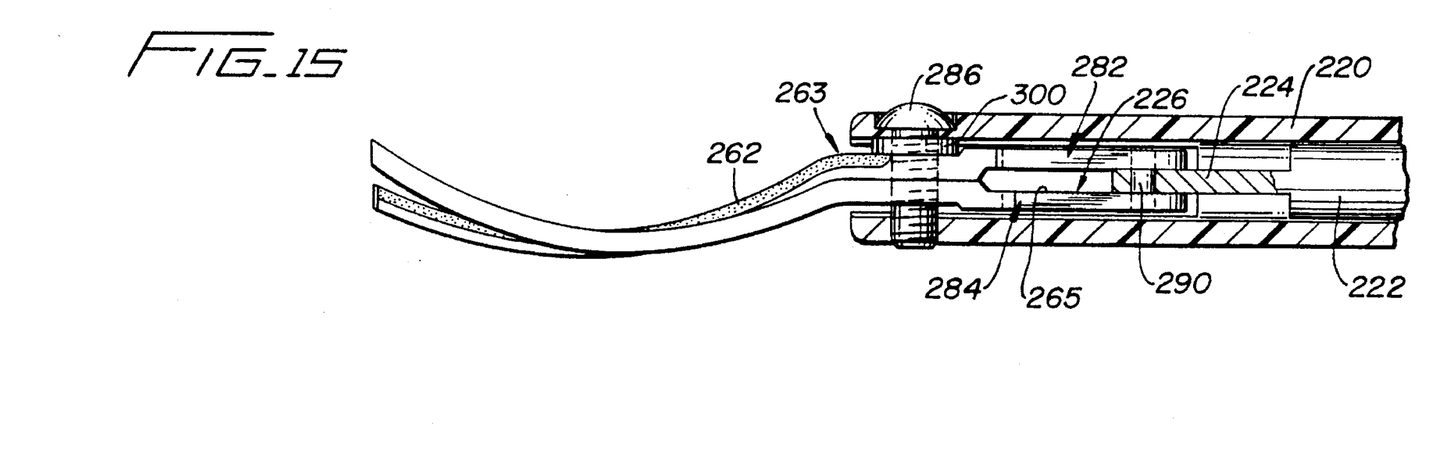
FIG. 15 is a top cutaway view of another tool mechanism for use in the bipolar surgical instrument of FIG. 8.
Figure 16:
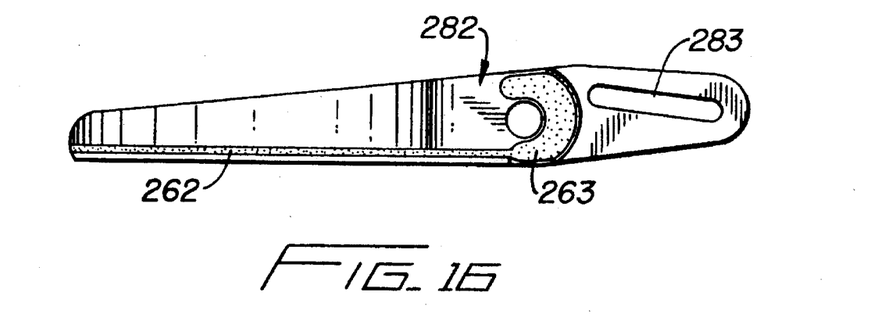
FIG. 16 is a side view of a first jaw member of the tool mechanism of FIG. 15.
Figure 17:
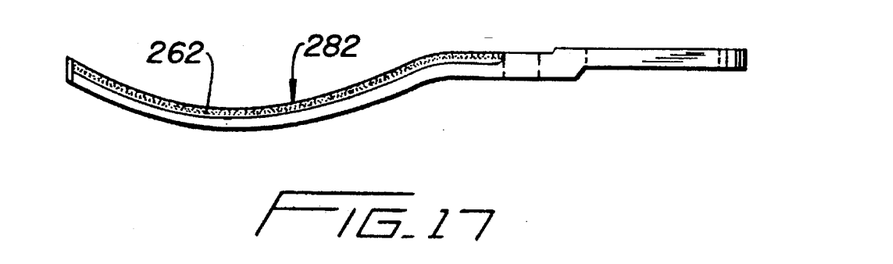
FIG. 17 is a top view of the jaw member of FIG. 16.
Figure 18:
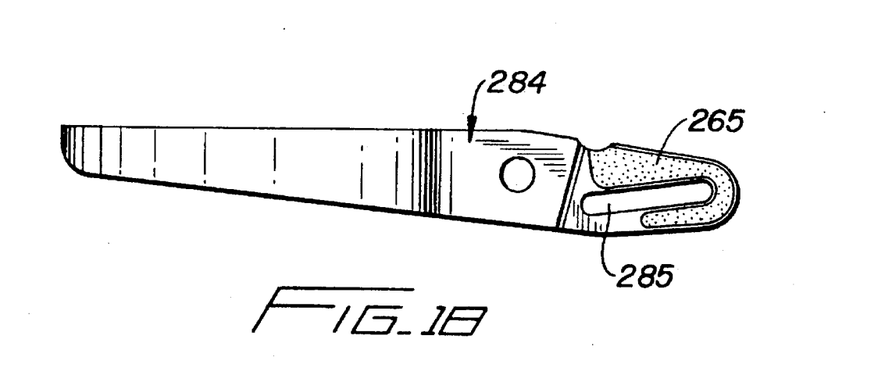
FIG. 18 is a side view of a second jaw member of the tool mechanism of FIG. 15.
Figure 19:
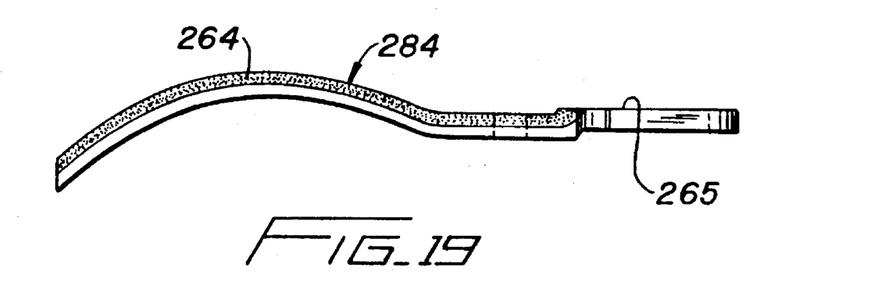
FIG. 19 is a top view of the jaw member of FIG. 18.

Another tool mechanism for use with the bipolar surgical instrument of FIGS. 1 or 8 is shown in FIG. 15. As in the previous embodiment, curved blade members 282 and 284 are employed. Referring to FIGS. 16–19, blade member 282 includes conductive pathway 262 and conductive region 263 as in the previous embodiment. Blade member 284 includes conductive pathway 264 and conductive region 265.

Referring back to FIG. 15, conductive pathway 262 communicates with outer tubular member through conductive region 263. Conductive region 263 communicates electrically with pivot pin 286. Washer 300 is optionally provided to help ensure electrical contact between the conductive region and the pivot pin.

Inner rod 222 terminates at its distal end in a single arm 224 which passes between legs 282 and 284. Electrical contact region 265 contacts arm 224 at surface 226 to provide power to conductive strip 264.

It will be apparent to those of skill in the art that, in addition to the configurations illustrated in the drawings for connecting the electrically conductive pathways to a source of electrical energy, numerous other such configurations are possible. For example, the inner surface of a camming slot can be plated with conductive material. Current flows from the inner rod to the camming slot through the bearing post at the distal end of the inner rod. The connection between the outer tube and the other conductive pathway could be selected from any of those shown above.

Alternatively, the conductive pathways can be fabricated from wire bonded to the blade members. The wire used to form the conductive pathways can be connected to the inner rod and the outer tubular member, or directly to the electrical receptacles, through any known technique. In short, any design permitting conductive pathways associated with insulating jaw members to be connected to a source of electrical energy is within the scope of the present invention.

It is also contemplated that one of the jaw members be fabricated entirely from conductive material. In this embodiment, the conductive jaw member is used as the return or ground electrode. Because the ground electrode is not powered by the electrosurgical generator, it does not generate as much heat as the current supplying electrode. Consequently, it is less likely to adhere to tissue or damage adjacent structures.

The insulating material used to form the jaw members of the abovedescribed tool mechanisms should preferably selected from ceramic, glass, or glass-ceramic materials. The selected material must be strong enough to function as a cutting tool and preferably be a poor thermal conductor to minimize instrument heating. Preferred materials include, but are not limited to zirconia, partially stabilized zirconia, aluminum oxide, silicon nitride and mixtures including these materials.

The material used for the conductive pathways and regions may be any metal having good electrical conductivity. Preferably, the selected metal possesses a coefficient of thermal expansion most nearly matching the coefficient of thermal expansion of the material selected to form the blades. Refractory metals such as nickel, molybdenum, tungsten, mixtures and conductive compositions containing these metals are suitable to form the conductive pathways. Other metals such as aluminum, stainless steel, gold, silver, copper, may also be employed in the conductive pathways.

The conductive pathways and conductive regions may be formed on the scissors blades through a variety of conventional metalizing coating techniques. Thick film techniques may be used, such as printing a conductive paste on the blades followed by firing to form the conductive pathways. Thin film techniques such as sputtering, evaporation, chemical vapor deposition, electroless plating and the like may also be employed to form the conductive pathways. Alternatively, the conductive pathways may be formed by positioning metal wires or strips along the blades followed by firing to bond the metal to the blade surfaces.

In use, the electrosurgical instrument of the present invention is connected to a suitable power supply through electrical connection receptacles 52 and 54. To actuate the tool mechanism 80, handle 16 is approximated towards handle 14, pivoting about pivot point 24. As the handles move, inner rod member 22 slides through outer tube 20 towards the distal end of the instrument. The longitudinal movement of rod 22 causes bearing post 90 to travel within longitudinal slot 83 of blade 82 while simultaneously travelling within angled cam slot 85 to cam blade 84 to a closed position. As blades 82 and 84 are approximated, electrical current sparks through tissue held between conductive pathways 62 and 64. The selected waveform, voltage, and current levels determine the type of electrical treatment performed, i.e., cutting, coagulation, or a combination of the two, as discussed above.

Use of the electrosurgical instrument of FIG. 8 is substantially similar to that of the electrosurgical instrument of FIG. 1.

It is understood that either or both of conductive pathways 62 and 64 may be used as a current-supplying electrode for the bipolar electrosurgical instrument of the present invention. For example, pathway 62 may be used to supply current to tissue and pathway 64 may be used as the return (or ground) electrode and vice versa.

The bipolar electrosurgical instrument of the present invention is a compact, lightweight and easy to use instrument incorporating many features required during endoscopic surgical procedures. The surgeon may advantageously manipulate the instrument with one hand, freeing his remaining hand for other purposes during the surgery. The present instrument overcomes many of the disadvantages encountered with prior art devices and provides a precision instrument which is easy to handle and simple to manufacture. As such, the instrument is readily adaptable for single use applications.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A bipolar electrosurgical instrument comprising:
   a handle assembly;
   a body portion attached to said handle assembly and extending distally therefrom;
   a tool mechanism operatively associated with a distal end of said body portion, said tool mechanism including first and second jaw members, each jaw member having a grooved portion formed therein, at least one of said jaw members movable between open and closed positions in response to movement of said handle assembly, said jaw members being fabricated from electrically insulating material;
   a first conductive pathway in said grooved portion of said first jaw member;
   a second conductive pathway in said grooved portion of said second jaw member, said first and second conductive pathways being electrically isolated from one another; and
   means for respectively electrically connecting said first and second conductive pathways to an electrical power supply.

2. A bipolar electrosurgical instrument according to claim 1 wherein said body portion comprises an inner rod coaxially slidable within an outer tube.

3. A bipolar electrosurgical instrument according to claim 2 wherein said inner rod and said outer tube are fabricated from electrically conductive material.

4. A bipolar electrosurgical instrument according to claim 3 wherein said means for electrically connecting said first and second conductive pathways to an electrical power supply comprises first and second electrical receptacles in said handle assembly.

5. A bipolar electrosurgical instrument according to claim 4 further comprising a first contact spring operatively associated with said first electrical receptacle and said inner rod and a second contact spring operatively associated with said second electrical receptacle and said outer tube, wherein said first contact spring connects said first electrical receptacle to said inner rod and said second contact spring connects said second electrical receptacle to said outer tube.

6. A bipolar electrosurgical instrument according to claim 5 wherein said inner rod electrically communicates with said first conductive pathway and said outer tube electrically communicates with said second conductive pathway.

7. A bipolar instrument according to claim 2 wherein said first and second jaw members are pivotally connected to one another.

8. A bipolar electrosurgical instrument according to claim 7 wherein one of said first and second jaw members is provided with an angled camming slot cooperating with a post member disposed on said inner rod member, wherein said angled Camming slot and said post member operate to aid in said movement between said open and closed positions.

9. A bipolar electrosurgical instrument according to claim 7 wherein both of said first and second jaw members are provided with angled camming slots, each of said camming slots cooperating with at least one post member disposed on said inner rod member, wherein said angled camming slots and said at least one post member operate to aid in said movement between said open and closed positions.

10. A bipolar electrosurgical instrument according to claim 1 wherein said first and second conductive pathways are configured and dimensioned such that current flows between said first and second pathways when said first and second jaw members are in an open position and such that current does not flow between said first and second pathways when said first and second jaw members are in a closed position.

11. A bipolar electrosurgical instrument according to claim 1 wherein said body portion is elongated and said handle assembly and tool mechanism are configured for endoscopic use.

12. A bipolar electrosurgical instrument according to claim 1 wherein said first and second jaw members are scissor blades having angled cutting surfaces.

13. A bipolar electrosurgical instrument according to claim 12 wherein said grooved portions are formed on said angled cutting surfaces.

14. A bipolar electrosurgical instrument according to claim 1 further comprising a rotatable member for rotating said first and second jaw members about a longitudinal axis of the instrument.

15. A bipolar electrosurgical instrument comprising:
   a handle assembly including electrical receptacle members for connection to a source of r.f. energy;
   an elongated body portion attached at one end to said handle assembly and extending distally therefrom, said elongated body portion including an inner rod member coaxially slidable within an outer tubular member;
   a tool mechanism operatively associated with a distal end of said elongated body portion and comprising a first electrically insulating jaw member pivotally connected to a second electrically insulating jaw member, at least one of said first and second jaw members movable between open and closed positions in response to movement of said handle assembly;
   a first conductive pathway communicating with said first electrically insulating jaw member and creating an electrical pathway with said inner rod member;
   a second conductive pathway communicating with said second electrically insulating jaw member and electrically communicating with said outer tubular member such that electrical current flows between said first and second conductive pathways when said first and second jaw members are in said open position and such that electrical current does not flow between said first and second conductive pathways when said first and second jaw members are in said closed position.

16. A bipolar electrosurgical instrument according to claim 15 wherein said first and second jaw members are scissors blades having angled cutting surfaces.

17. A bipolar electrosurgical instrument according to claim 16 wherein said first and second conductive pathways are respectively formed within grooves on said angled cutting surfaces.

18. A bipolar electrosurgical instrument according to claim 15 further comprising a rotatable member for rotating said first and second jaw members about a longitudinal axis of the instrument.

19. In a bipolar electrosurgical instrument of the type having pivotally connected, relatively movable blade members having at least one cutting surface, the improvement comprising:
   first and second blade members formed from electrically insulating material, said first blade member having a first conducting strip formed on said cutting surface, and said second blade member having a second conducting strip formed on said cutting surface, said first and second conductive strips being electrically isolated from one another.

20. A bipolar electrosurgical instrument as recited in claim 19, wherein said first and said second blade members and said first and second conducting strips each include a surface area, the surface area of said first conducting strip being less than 30% of the surface area of said first blade member and the surface area of said second conducting strip being less than 30% of the surface area of said second blade member.

21. A bipolar electrosurgical instrument as recited in claim 19 wherein said first and second blade members define respective first and second longitudinal axes and said first and second conducting strips respectively extend substantially parallel to said first and second longitudinal axes.

22. An endoscopic bipolar electrosurgical instrument comprising;
   an elongated endoscopic member having proximal and distal ends;
   a handle assembly attached at said proximal end of said elongated endoscopic member;
   first and second jaw members pivotally attached at said distal end of said elongated endoscopic member, said first and second jaw members composed of electrically insulating material and having a planar angled exterior surface portion and an exterior edge;
   a first conductive strip disposed on said planar angled surface portion of said first jaw member at least over an entire length of said planar angled surface portion and spaced from the exterior edge of said first jaw member;
   a second conductive strip disposed on said planar angled surface portion of said second jaw member at least over an entire length of said planar angled surface portion and spaced from the exterior edge of said second jaw member; and
   actuating means extending from said handle assembly to said first and second jaw members to move at least one of said first and second jaw members between open and closed positions.

23. In a bipolar electrosurgical instrument of the type having pivotally connected, relatively movable jaw members, the jaw members each having an internal surface, the improvement comprising:
   first and second jaw members formed from electrically insulating material, said first jaw member having a first conducting strip formed on said internal surface, and said second jaw member having a second conducting strip formed on said internal surface.

* * * * *